United States Patent
Schmidt et al.

(10) Patent No.: US 11,547,817 B2
(45) Date of Patent: Jan. 10, 2023

(54) EVAPORATOR UNIT FOR AN INHALER HAVING A WICK STRUCTURE WITH A SHAFT AND A COLLAR

(71) Applicant: KÖRBER TECHNOLOGIES GMBH, Hamburg (DE)

(72) Inventors: Rene Schmidt, Buchholz I.D.N. (DE); Marc Kessler, Hamburg (DE); Gunnar Niebuhr, Hamburg (DE); Karen Kalaydzhyan, Hamburg (DE)

(73) Assignee: KÖRBER TECHNOLOGIES GMBH, Hamburg (DE)

( * ) Notice: Subject to any disclaimer, the term of this patent is extended or adjusted under 35 U.S.C. 154(b) by 237 days.

(21) Appl. No.: 16/755,678

(22) PCT Filed: Oct. 10, 2018

(86) PCT No.: PCT/EP2018/077601
§ 371 (c)(1),
(2) Date: Apr. 13, 2020

(87) PCT Pub. No.: WO2019/072915
PCT Pub. Date: Apr. 18, 2019

(65) Prior Publication Data
US 2021/0186097 A1    Jun. 24, 2021

(30) Foreign Application Priority Data

Oct. 13, 2017   (DE) .......................... 102017123870.0

(51) Int. Cl.
*A61M 15/06*       (2006.01)
*A24F 40/44*       (2020.01)
(Continued)

(52) U.S. Cl.
CPC ............. *A61M 15/06* (2013.01); *A24F 40/44* (2020.01); *A24F 40/485* (2020.01); *A24F 40/10* (2020.01); *A24F 40/42* (2020.01); *A24F 40/46* (2020.01)

(58) Field of Classification Search
CPC .......... A24F 40/10; A24F 40/44; A24F 40/46; A24F 40/42; A24F 40/485; A61M 15/06
See application file for complete search history.

(56) References Cited

U.S. PATENT DOCUMENTS

| | | |
|---|---|---|
| 6,585,509 B2 | 7/2003 | Young et al. |
| 6,634,864 B1 | 10/2003 | Young et al. |

(Continued)

FOREIGN PATENT DOCUMENTS

| | | |
|---|---|---|
| AT | 507 187 A4 | 10/2008 |
| CN | 204104843 U | 1/2015 |

(Continued)

OTHER PUBLICATIONS

Communication received from the U.S. Patent Office dated Jul. 15, 2021 regarding a Third Party Submission submitted to the U.S. Patent Office on July 9, 2921.

(Continued)

*Primary Examiner* — Hae Moon Hyeon
(74) *Attorney, Agent, or Firm* — Saliwanchik, Lloyd & Eisenschenk

(57) ABSTRACT

The invention relates to an evaporator unit for an inhaler, in particular an electronic cigarette product, comprising an electrically operable heating body, in particular a flat heating body, which has an inlet side and an outlet side, and a plurality of microchannels, each of which extends from the inlet side to the outlet side through the heating body. The heating body is designed to evaporate liquid being transferred through the microchannels by applying a heating (Continued)

voltage. A porous and/or capillary wick structure is arranged on the inlet side of the heating body, said wick structure being fluidically connected or connectable to a liquid store. The wick structure has a shaft which extends through a passage opening of the support, and a collar, which is arranged between the support and the heating body, wherein the diameter of the collar is greater than the diameter of the passage opening of the support.

19 Claims, 4 Drawing Sheets

(51) Int. Cl.
  *A24F 40/485* (2020.01)
  *A24F 40/10* (2020.01)
  *A24F 40/46* (2020.01)
  *A24F 40/42* (2020.01)

(56) References Cited

U.S. PATENT DOCUMENTS

| | | |
|---|---|---|
| 11,154,666 B2 * | 10/2021 | Schmidt ............... A61M 11/042 |
| 2009/0220222 A1 | 9/2009 | Rabin et al. |
| 2009/0224064 A1 | 9/2009 | Brodbeck et al. |
| 2009/0324206 A1 | 12/2009 | Young et al. |
| 2011/0226236 A1 | 9/2011 | Buchberger |
| 2015/0059780 A1 | 3/2015 | Davis |
| 2016/0262454 A1 | 9/2016 | Sears et al. |
| 2016/0338410 A1 † | 11/2016 | Batista |
| 2016/0345630 A1 | 12/2016 | Mironov et al. |
| 2016/0353801 A1 | 12/2016 | Zinovik et al. |
| 2017/0106113 A1 † | 4/2017 | Meinhart |
| 2018/0249763 A1 | 9/2018 | Schmidt |
| 2019/0328039 A1 * | 10/2019 | Romming ............. A24F 40/485 |
| 2020/0008473 A1 * | 1/2020 | Schmidt ................ A61M 15/06 |
| 2020/0120983 A1 | 4/2020 | Chen |
| 2020/0260788 A1 * | 8/2020 | Cornils ................. A24F 40/485 |
| 2021/0037886 A1 | 2/2021 | Mironov et al. |
| 2021/0186100 A1 * | 6/2021 | Trieu ...................... A24F 40/42 |
| 2021/0195952 A1 * | 7/2021 | Trieu ...................... A24F 40/46 |

FOREIGN PATENT DOCUMENTS

| | | |
|---|---|---|
| CN | 204499489 U | 7/2016 |
| EP | 3 117 860 A1 | 10/2009 |
| EP | 3 372 096 A1 | 3/2018 |
| JP | 2017-506509 A | 3/2017 |
| WO | WO 2015/077645 A1 | 5/2015 |
| WO | WO 2015/117701 A1 | 8/2015 |
| WO | WO 2016/096780 A1 | 6/2016 |
| WO | WO 2017/139963 A1 | 8/2017 |
| WO | WO 2018/083007 A1 | 5/2018 |

OTHER PUBLICATIONS

Third-Party Submission under 37 CFR 1.290 and concise description of relevance.
1st Examination Report issued by the German Patent and Trademark Office with respect to the priority German Patent Application No. 10 2017 123 870.0.
Office Action issued by the Japanese Patent Office dated Nov. 25, 2022 for parallel Japanese patent application No. 2020-520574.

* cited by examiner
† cited by third party

EVAPORATOR UNIT FOR AN INHALER HAVING A WICK STRUCTURE WITH A SHAFT AND A COLLAR

CROSS REFERENCE TO RELATED APPLICATIONS

This application is a National Stage Application of International Application Number PCT/EP2018/077601, filed Oct. 10, 2018; which claims priority to German Patent Application No. 10 2017 123 870.0, filed Oct. 13, 2017.

FIELD OF INVENTION

The present invention relates to an evaporator unit for an inhaler, in particular for an electronic cigarette product, comprising an electrically operable heating body, in particular a flat heating body, which has an inlet side and an outlet side, and a plurality of microchannels, each of which extends from the inlet side to the outlet side through the heating body, the heating body being designed to evaporate liquid being transferred through the microchannels by applying a heating voltage.

BACKGROUND OF THE INVENTION

In the prior art, the liquid supply to the heating body typically takes place in a capillary manner by means of a wick. The wicks used ideally have a constant transfer effect along the transfer direction. If the transfer rate is lower than the required evaporation rate, the wick dries out in close proximity to the heating body. A dry puff follows and harmful substances are released.

In the case of a flat heating body, the heating body must be wetted by the wick as evenly as possible at all times and in every location in order to ensure a constant temperature distribution and thus uniform, pollutant-free evaporation over its surface.

BRIEF SUMMARY OF THE INVENTION

The object of the invention is to provide an evaporator unit which is functionally reliable at all times and has high thermo-electromechanical stability, with which the formation of harmful substances during the evaporation of the liquid can be avoided.

The invention achieves said object by means of the features of the independent claims.

According to the invention, a porous and/or capillary wick structure is arranged on the inlet side of the heating body and is fluidically connected or connectable to a liquid store. The wick structure has a shaft extending through a passage opening of the support and a circumferential collar arranged between the support and the heating body. According to the invention, the diameter of the collar is larger than the diameter of the passage opening of the support. The collar can therefore rest on the part of the support forming the passage opening and in this way hold the wick structure, since the collar cannot migrate through the passage opening in the direction of the liquid store due to the dimensions according to the invention, which would impair the functionality of the evaporator unit.

At least one preload-generating clamping element is preferably provided, which is arranged and set up for clamping the heating body and the collar onto the support. By means of the clamping element, the collar of the wick structure is clamped between the heating body and the support and in this way the wick structure is held securely and immovably in the evaporator unit. In this case, it is particularly advantageous if the collar protrudes over its entire circumference through the passage opening of the support, preferably with a protrusion of at least 0.1 mm or more. The protrusion on all sides ensures uniform clamping and prevents leakage.

In a particularly preferred embodiment, the at least one clamping element simultaneously serves as an electrode for electrically contacting and supplying the heating body. In this case, separate electrodes for the electrical contacting of the heating body are unnecessary.

At least two clamping elements are preferably provided on opposite sides of the heating body, which allows for particularly high mechanical stability with relatively little effort. In a preferred embodiment, the at least one clamping element has a clamping bracket which makes linear contact with the heating body. Due to the line contact between the clamping bracket and the heating body, there is an excellent electrical connection between the clamping element and the heating body, simultaneously with ideal thermal decoupling between the clamping element and the heating body due to the lack of surface contact.

The clamping element can clamp the heating body laterally parallel to the outlet side and/or perpendicularly to the outlet side and/or in a groove or step of the support. The latter option involves two contact lines between the clamping bracket and the heating body, which further improves the electrical contacting considerably. A clamping element can also have more than one clamping bracket, in particular any two or all three clamping brackets of the aforementioned type.

In an advantageous embodiment, at least one electrical conductor, which extends through a bore in the support, can be provided for electrically contacting the clamping element, and in particular contacts a printed circuit board which is arranged at a distance on the side of the support facing away from the heating body. However, it is also advantageously possible for the support itself to be designed as a printed circuit board, which reduces the number of parts and thus the manufacturing outlay.

After all, a particularly flat silicon heater is advantageously provided, which clamps the wick structure onto the support in such a way that the wick structure is mechanically fixed, a secure air-impermeable hydraulic coupling is created between the heating body and the liquid reservoir, and at the same time the electrical coupling of the heating body is ensured. The heating body and reservoir are on opposite sides of the wick.

The collar can advantageously be a plate, a flange or a collar which is circumferential in another plane. In the case of a plate, the wick structure is thus mushroom-shaped. The collar according to the invention allows the wick structure to be clamped between the support and the heating body while at the same time conducting liquid through the passage opening of the support. The heating body is thermally insulated from the support by the wick structure;

at the same time the clamping by electrical conductors also provides the heating body with power. The electrical connection exerts a contact pressure on the heating body and wick structure, which counteracts thermal pressures during evaporation.

What is essential is a liquid-conducting system between a wick surface and a surface of the heating body, which can advantageously include the collar, but does not necessarily have to. The support can also be formed, for example, by an optionally widened housing wall of the liquid reservoir. In this case, a separate support may not be necessary.

The formation of bubbles in the inlet region of the heating body can be counteracted by means of the wick structure. Bubbles that form in the microchannels of the heating body cannot penetrate into the region upstream from the inlet side and lead to a dry-running of the inlet region of the heating body and thus to a functional impairment of the evaporator. Any bubbles in the region of the wick structure are trapped in the pores or capillaries thereof and cannot form large bubbles. It is important here that the wick structure lies flat and in contact with the heating body on the inlet side and covers all microchannels on the inlet side so that individual bubbles that form in the microchannels cannot exit the microchannels in the wrong direction, namely on the inlet side towards the liquid store. Rather, the blockage of the inlet side by the wick structure according to the invention ensures that bubbles forming in the microchannels migrate in the microchannels to the outlet side, where they are expelled from the microchannels and can then no longer cause any problems.

In this case, the duration of the individual evaporation steps at different temperatures and/or an evaporation of the individual components of the individual portions of the liquid can be kept so short and/or clocked using an activation frequency that the step-by-step evaporation cannot be perceived by a consumer and nevertheless a largely homogeneous, repeatable, precise aerosol formation having good taste conformity can be ensured. In particular, it is advantageous to first evaporate a low-boiling component of the liquid in a first evaporation interval at a first temperature A, and then to evaporate a high-boiling component of the liquid in a second evaporation interval at a second temperature B, which exceeds temperature A.

The transfer rate of the wick structure is advantageously at least as large as the maximum evaporation rate of the heating body. This ensures adequate liquid tracking at all times so that a disadvantageous dry-running of the heating body is prevented. The evaporation rate is determined by the geometry of the heating body structure (volume vs. surface) and the evaporator output.

Accordingly, the capillary wick structure is set up to transfer the liquid evenly over the entire volume thereof to the heating body. The transfer rate of the wick structure and the evaporation rate of the heating body are set in relation to one another such that the transfer rate can operate at least the rate of evaporation. This prevents too little liquid from being present on the heating body during the evaporation process, which would dry said heating body out.

The wick structure can consist of any sufficiently heat-resistant, porous and/or capillary material having a suitable transfer rate. The wick structure can advantageously consist wholly or partially of cotton, cellulose, acetate, glass fibre fabric, glass fibre ceramic, sintered ceramic, ceramic paper, aluminosilicate paper, metal foam, metal sponge, and/or a composite of two or more of the aforementioned materials.

BRIEF DESCRIPTION OF THE FIGURES

The invention will be explained below on the basis of the preferred embodiments with reference to the accompanying drawings. In the drawings.

DETAILED DESCRIPTION

Figure 1:
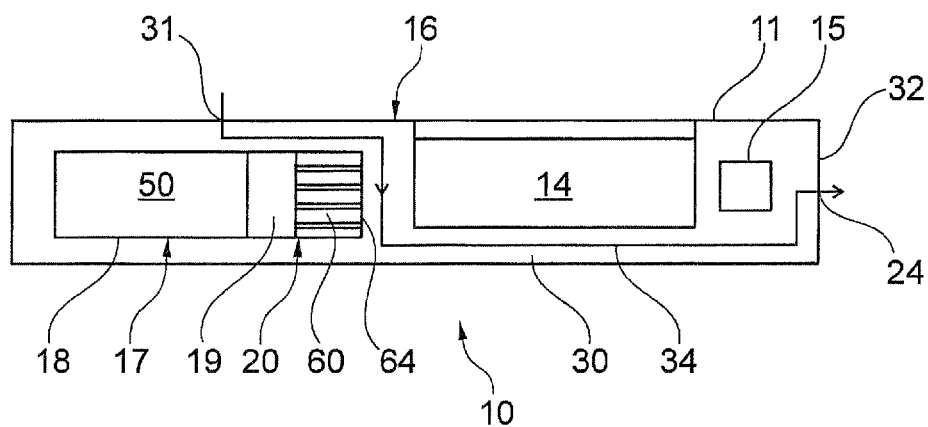
FIG. 1 is a schematic representation of an electronic cigarette product.

The inhaler 10, in this case an electronic cigarette product, comprises a housing 11 in which an air channel 30 is provided between at least one air inlet opening 31 and one air outlet opening 24 at a mouth end 32 of the inhaler 10. The mouth end 32 of the inhaler 10 is the end at which the consumer puffs for the purpose of inhalation and thereby applies a negative pressure to the inhaler 10 and generates an air flow 34 in the air channel 30.

The inhaler consists advantageously of a base part 16 and a consumption unit or cartridge 17, which comprises the evaporator unit 20 and the liquid store 18 and is designed in particular in the form of an exchangeable cartridge. The air sucked in through the air inlet opening 31 is conducted in the air channel 30 to or along at least one evaporator unit 20. The evaporator unit 20 is connected or can be connected to at least one liquid store 18 in which at least one liquid 50 is stored. The evaporator unit 20 evaporates liquid 50, which is supplied thereto from the liquid store 18, and adds the evaporated liquid as aerosol/vapour 22 (see FIG. 3) into the air flow 34 at an outlet side 64. An advantageous volume of the liquid store 18 lies in the range between 0.1 ml and 5 ml, preferably between 0.5 ml and 3 ml, more preferably between 0.7 ml and 2 ml or 1.5 ml.

The electronic cigarette also comprises an electrical energy store 14 and an electronic control device 15. The energy store 14 is usually arranged in the base part 16 and can be, in particular, a disposable electrochemical battery or a rechargeable electrochemical battery, for example a lithium-ion battery. The electronic control device 15 comprises at least one digital data processing apparatus, in particular a microprocessor and/or microcontroller, in the base part 16 (as shown in FIG. 1) and/or in the consumption unit or cartridge 17.

A sensor, such as a pressure sensor or a pressure switch or flow switch, is advantageously arranged in the housing 11, wherein the electronic control device 15 can determine, on the basis of a sensor signal output from the sensor, that a consumer is puffing the cigarette product 10 at the mouth end 32 in order to inhale. In this case, the electronic control device 15 triggers the evaporator unit 20 to add liquid 50 from the liquid store 18 as aerosol/vapour into the air flow 34.

The liquid 50 stored in the liquid store 18 to be dosed is, for example, a mixture of 1,2-propylene glycol, glycerol, water, at least one flavour and/or at least one active substance, in particular nicotine.

The consumption unit or cartridge 17 advantageously comprises a non-volatile data store for storing information or parameters relating to the consumption unit or cartridge 17. The data store may be part of the electronic control device 15. The data store is advantageously used to store information regarding the composition of the liquid stored in the liquid store 18, information regarding the process profile, in particular power/temperature control; data for condition monitoring or system testing, for example seal testing; data regarding copy protection and counterfeit protection, an ID for unique identification of the consumption unit or cartridge 17, serial number, date of manufacture and/or expiry date, and/or number of puffs (number of inhalation puffs by the consumer) or the period of use. The data store is advantageously connected or can be connected to the electronic control unit 15 by means of contacts and/or conducts.

Figure 2:
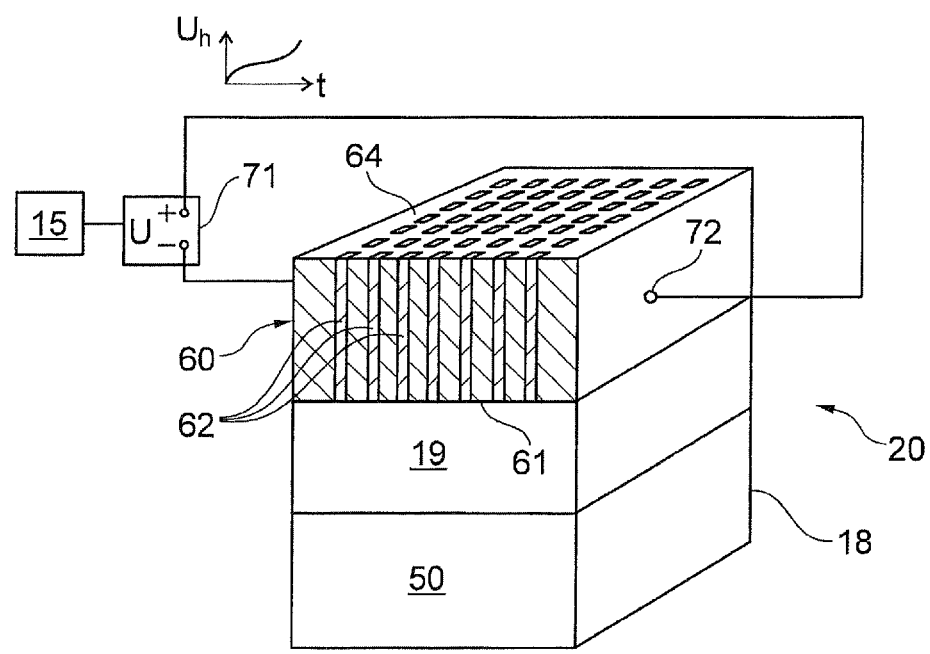
FIG. 2 is a perspective cross-sectional view of an evaporator unit.

An advantageous embodiment of an evaporator unit 20 according to the invention is shown in FIG. 2. The evaporator unit 20 comprises a block-shaped, preferably monolithic heating body 60, preferably made of an electrically conductive material, preferably silicon, doped ceramic, metal ceramic, filter ceramic, semiconductor, in particular germanium, graphite, semimetal and/or metal. It is not necessary for the entire heating body 60 to be made of an electrically conductive material. It may be sufficient, for example, that the surface of the heating body 60 is coated in an electrically conductive manner, for example has a metallic coating. In this case, the entire surface does not have to be coated; for example, conductor tracks can be provided on a non-conductive base body.

The heating body 60 is provided with a plurality of microchannels 62, which fluidically connect an inlet side 61 of the heating body 60 to an outlet side 64. The inlet side 61 is fluidically connected to the liquid store 18 via a wick structure 19. The wick structure 19 is used for the passive transfer of liquid from the liquid store 18 to the heating body 60 by means of capillary forces. The wick structure 19, in the region that contacts the inlet side 61 of the heating body 60, serves to distribute liquid evenly, to be temperature-resistant and to form a kind of check valve with its relatively small pores and/or thin capillaries in order to prevent undesirable backflow of bubbly liquid from the heating body 60 into the wick structure 19 and/or into the liquid store 18.

The median diameter of the microchannels 62 is preferably in the range between 5 μm and 200 μm, more preferably in the range between 30 μm and 150 μm, even more preferably in the range between 50 μm and 100 μm. Due to these dimensions, a capillary effect is advantageously produced, so that liquid penetrating into a microchannel 62 at the inlet side 61 rises upwards through the microchannel 62 until the microchannel 62 is filled with liquid. The volume ratio of the microchannels 62 to the heating body 60, which can be referred to as the porosity of the heating body 60, is for example in the range between 10% and 50%, advantageously in the range between 15% and 40%, further advantageously in the range between 20% and 30%, and is, for example, 25%.

The edge lengths of the surfaces of the heating body 60 provided with microchannels 62 are, for example, in the range between 0.5 mm and 3 mm. For example, the dimensions of the surfaces of the heating body 60 provided with microchannels 62 can be as follows: 0.95 mm×1.75 mm; 1.9 mm×1.75 mm or 1.9 mm×0.75 mm. The edge lengths of the heating body 60 can be, for example, in the range between 0.5 mm and 5 mm, preferably in the range between 0.75 mm and 4 mm, more preferably in the range between 1 mm and 3 mm. The surface of the heating body 60 (chip size) can be, for example, 1 mm×3 mm or 2 mm×3 mm.

The width b of the heating body 60 (see FIG. 6) is preferably in the range between 1 mm and 5 mm, more preferably in the range between 2 mm and 4 mm, and is, for example, 3 mm. The height h of the heating body 60 (see FIG. 6) is preferably in the range between 0.05 mm and 1 mm, more preferably in the range between 0.1 mm and 0.75 mm, even more preferably in the range between 0.2 mm and 0.5 mm, and is, for example, 0.3 mm.

The number of microchannels 62 is preferably in the range between four and 1000. This allows the heat input from the support into the microchannels 62 to be optimised and ensures a high evaporation capacity and a sufficiently large vapour outlet surface.

Figure 3:
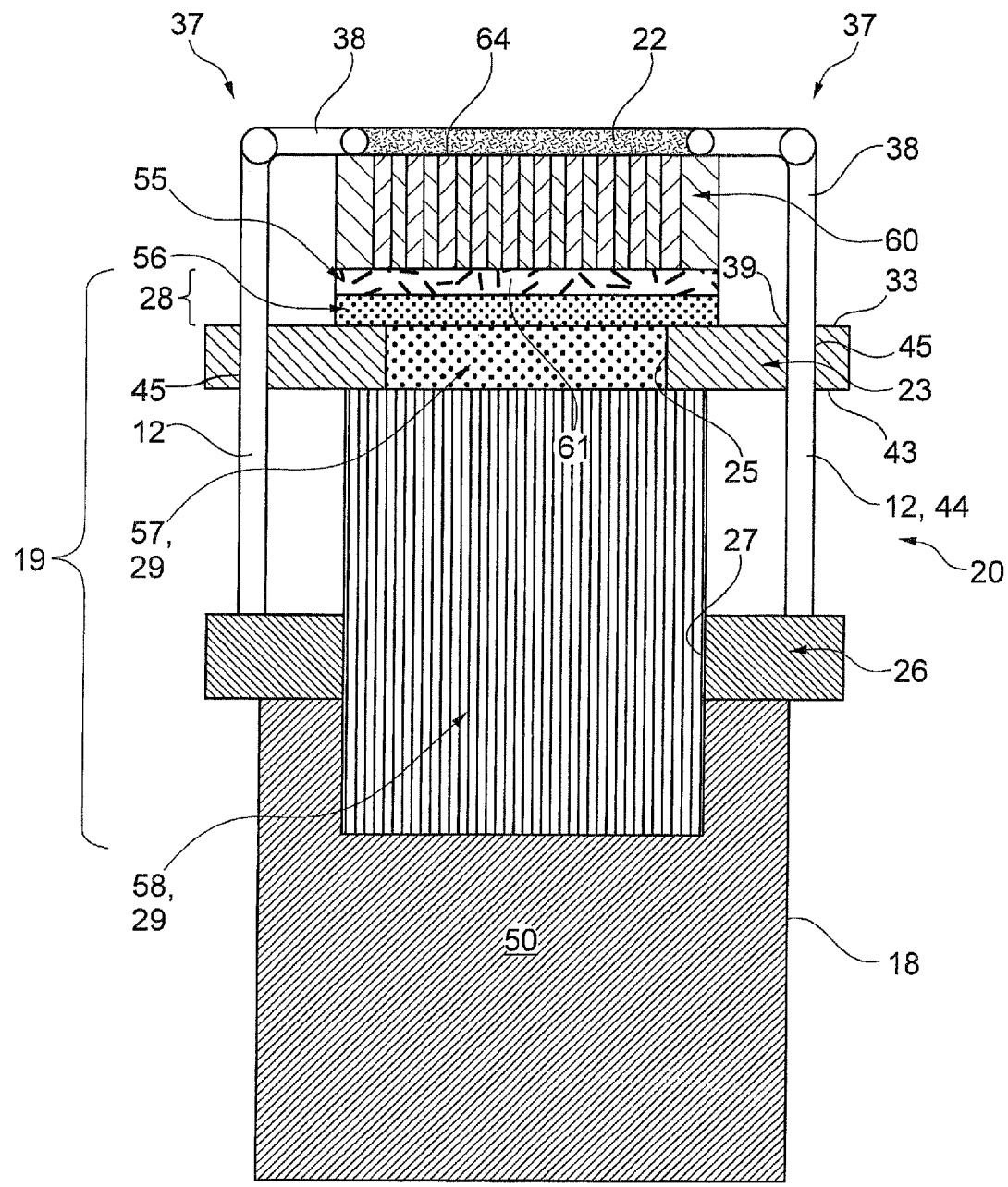
FIG. 3 is a schematic cross-sectional view of an evaporator unit in an embodiment of the invention.

The microchannels 62 are arranged in the form of a square, rectangular, polygonal, round, oval or differently shaped array, as can be seen in FIG. 3. The array may be in the form of a matrix having w columns and z rows, wherein w is advantageously in the range between 2 and 50 and further advantageously in the range between 3 and 30 and/or z is advantageously in the range between 2 and 50 and further advantageously in the range between 3 and 30. This allows for an effective and easily manufactured arrangement of microchannels 62 having a guaranteed high evaporation capacity.

The cross section of the microchannels 62 can be square, rectangular, polygonal, round, oval or otherwise shaped and/or can vary lengthwise in portions, in particular may increase, decrease or remain constant.

The length of one or each microchannel 62 is preferably in the range between 100 μm and 1000 μm, more preferably in the range between 150 μm and 750 μm, even more preferably in the range between 180 μm and 500 μm, and is, for example, 300 μm. This allows an optimum liquid absorption and a portion formation with sufficient heat input from the heating body 60 into the microchannels 62.

The distance between two microchannels 62 is preferably at least 1.3 times the clear diameter of one microchannel 62, wherein the distance refers to the centre axes of the two microchannels 62. The distance can preferably be 1.5 to 5 times the clear diameter of a microchannel 62, more preferably 2 to 4 times. In this way, an optimal heat input from the support into the microchannels and a sufficiently stable arrangement and wall thickness of the microchannels can be realised.

The evaporator unit 20 has a heating voltage source 71, preferably controllable by the electronic control device 15, which is connected via electrodes 72 to opposite sides of the heating body 60, in such a manner that an electrical voltage Uh produced by the heating voltage source 71 leads to a current flow through the heating body 60. Due to the ohmic resistance of the electrically conductive heating body 60, the current flow leads to heating of the heating body 60 and therefore to evaporation of the liquid 50 contained in the microchannels 62. The heating body 60 thus acts as an evaporator. The vapour/aerosol generated in this manner escapes to the outlet side 64 from the microchannels 62 and is added to the air flow 34, see FIG. 1. More precisely, upon detection of an air stream 34 caused by the consumer puffing through the air channel 30, the control device 15 controls the heating voltage source 71, wherein the liquid 50 in the microchannels 62 is driven out of the microchannels 62 in the form of vapour/aerosol by spontaneous heating.

A voltage curve Uh(t) adjusted to the liquid mixture used is preferably stored in the data store of the inhaler 10. This makes it possible to set the voltage curve Uh(t) according to the liquid 50 used, so that the heating temperature of the heating body 60, and therefore also the temperature of the capillary microchannels 62, can be controlled in accordance with the known evaporation kinetics of the respective liquid 50 over time during the evaporation procedure, thus achieving optimum evaporation results. The evaporation temperature is preferably in the range between 100° C. and 400° C., more preferably between 150° C. and 350° C., even more preferably between 190° C. and 290° C.

The heating body 60 can be advantageously manufactured from parts of a wafer using thin film layer technology, which has a layer thickness of preferably less than or equal to 1000 µm, more preferably less than or equal to 750 µm, even more preferably less than or equal to 500 µm. Surfaces of the heating body 60 can advantageously be hydrophilic. The outlet side 64 of the heating body 60 can advantageously be microstructured or have microgrooves.

The evaporator unit 20 is set in such a manner that a quantity of liquid is added preferably in the range between 1 µl and 20 µl, more preferably between 2 µl and 10 µl, even more preferably between 3 µl and 5 µl, typically 4 µl per puff by the consumer. The evaporator unit 20 can preferably be adjustable in terms of the amount of liquid/vapour per puff.

A porous and/or capillary, liquid-conducting wick structure 19 is arranged on the inlet side 61 of the heating body 60. The wick structure 19 contacts the inlet side 61 of the heating body 60 flatly and covers all microchannels 62 on the inlet side 61, as can be seen in FIGS. 2, 3, 6 and 8. On the side opposite the heating body 60, the wick structure 19 is fluidically connected to the liquid store 18. The direct connection of the liquid store 18 to the wick structure 19 shown in FIGS. 1 to 3 is only to be understood as an example. In particular, a liquid interface and/or a plurality of liquid conduits can be provided between the liquid store 18 and the wick structure 19. The liquid store 18 can therefore also be arranged at a distance from the wick structure 19. The dimensions of the liquid store 18 can be larger than those of the wick structure 19, see for example FIG. 3. The wick structure 19 can, for example, be inserted into an opening in a housing of the liquid store 18. A plurality of evaporator units 20 can also be associated with a liquid store 18.

The wick structure 19 consists of porous and/or capillary material which, due to capillary forces, is able to passively transfer sufficient liquid evaporated from the heating body 60 from the liquid store 18 to the heating body 60 in order to prevent the microchannels 62 from running empty and to prevent problems resulting therefrom.

The wick structure 19 consists advantageously of a non-conductive material in order to avoid an undesired heating of the liquid in the wick structure 19 by current flow. If the wick structure 19 consists of a conductive material, which is not excluded, an insulating layer of an electrically and/or thermally insulating material, for example glass, ceramic or plastics material, is advantageously provided between the wick structure 19 and the heating body 60, with passage openings extending through the insulating layer and corresponding to the microchannels 62.

The wick structure 19 consists advantageously of one or a plurality of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, or a combination of two or a plurality of the materials mentioned above. In an advantageous practical embodiment, the wick structure 19 may comprise at least one ceramic fibre paper and/or one porous ceramic. The volume of the wick structure 19 is preferably in the range between 1 $mm^3$ and 10 $mm^3$, more preferably in the range between 2 $mm^3$ and 8 $mm^3$, even more preferably in the range between 3 $mm^3$ and 7 $mm^3$ and is, for example, 5 $mm^3$.

Advantageous embodiments of an evaporator unit 20 are shown in FIGS. 3 to 8. The wick structure 19 can generally be in one part, see FIG. 8, or in several parts, see FIGS. 3 and 6.

Figure 6:
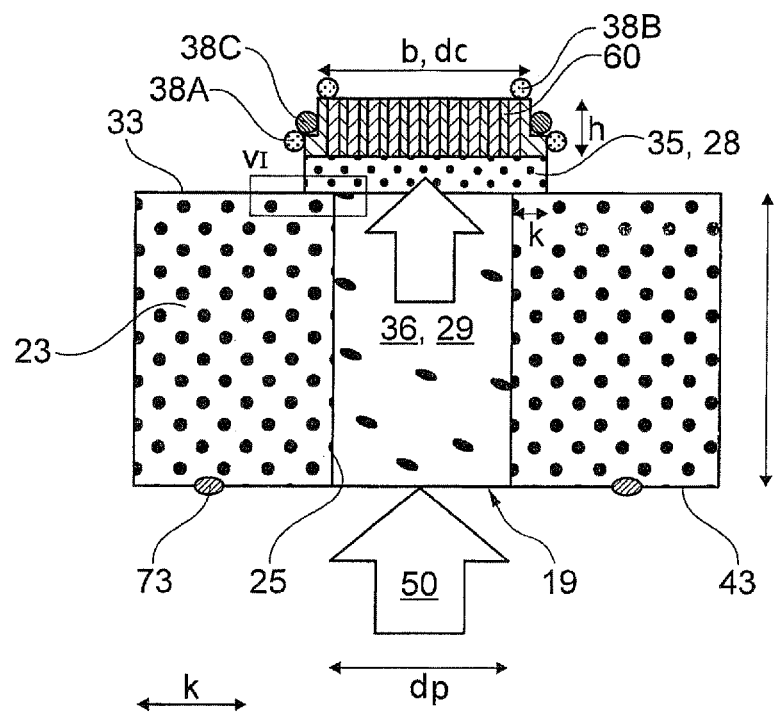
FIG. 6, 8 are cross-sectional views of an evaporator unit in further embodiments of the invention.
Figure 7:
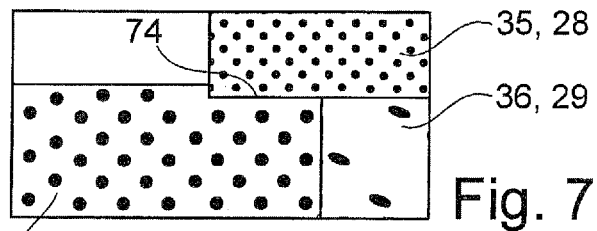
FIG. 7 is a section from FIG. 6 in the region of the protrusion of the wick collar over the passage opening of the support.

In the embodiment according to FIG. 6, the wick structure 19 is two-layered, for example, having a wick layer 35 which rests in flat contact on the inlet side 61 of the heating body 60, and a further wick layer 36 in flat contact thereon. The wick layer 35 may preferably be a fibre paper or ceramic paper layer, with or without a glass filter. The further wick layer 36 may preferably be a porous ceramic.

In the embodiment according to FIG. 3, the wick structure 19 comprises more than two layers, for example, four layers. A filter layer 55 is arranged directly adjacent to the heating body 60 and makes contact flatly therewith, which filter layer can consist in particular of one, two or more microglass fibre layers. A fibrous paper layer 56 can be arranged adjacently thereto. Adjacent to this region, wick layers 57, 58 are advantageously provided, for example a ceramic wick layer 57 and an oil lamp wick layer 58, i.e. a glass fibre wick material which is conventionally used for the wicks of oil lamps.

The capillary forces for the capillary transfer of liquid from the liquid store 18 to the heating body 60 can be provided predominantly or completely by the wick layers 57, 58. It is generally not necessary that all layers of the wick structure 19 provide capillary forces for the capillary transfer of the liquid. It may also be sufficient that only one layer of the wick structure 19 provides capillary forces for the capillary transfer of the liquid.

The evaporator unit 20 has an in particular plate-shaped support 23 for supporting the heating body 60 and/or the wick structure 19, as shown in FIGS. 3 to 8. The support 23 can consist of a suitable material, for example ceramic, glass and/or plastics material, including fibre-reinforced plastics, for example printed circuit board material, and has a passage opening 25, through which the wick structure 19 extends and in which the wick structure 19 is held.

The thickness D of the support 23 (see FIG. 6) is preferably in the range between 0.5 mm to 4 mm, more preferably in the range between 1 mm to 3 mm, even more preferably in the range between 1 mm and 2 mm and can be, for example, 1.6 mm or 2 mm. The thickness of a wick layer 57 arranged in the passage opening 25 of the support 23 can be adapted to the thickness of the support 23 or correspond to it and therefore also be 1.6 mm or 2 mm, for example.

The passage opening 25 is advantageously circular, which is easy to manufacture. The diameter d, or possibly the mean diameter, of the passage opening 25 (see FIG. 6) is preferably in the range between 0.5 mm and 4 mm, preferably in the range between 1 mm and 3 mm, more preferably in the range between 1.5 mm and 2.5 mm and is, for example, 2 mm.

The diameter d of the passage opening 25 is smaller or the same, advantageously smaller than the width b of the heating body 60, see FIG. 6. The volume of the passage opening 25, or the wick volume in the passage opening 25, is advantageously in the range between 1 $mm^3$ and 8 $mm^3$, preferably in the range between 2 $mm^3$ and 6.5 $mm^3$, more preferably in the range between 2.5 $mm^3$ and 5 $mm^3$.

The wick structure 19 has a collar-shaped portion or collar 28 and a shaft portion or shaft 29, or consists of these components 28, 29.

The collar 28 is arranged between the heating body 60 and the support 23, is in flat contact with the heating body 60 on the inlet side 61 and thereby covers all the microchannels 62. The thickness s of the collar (see FIG. 8) is advantageously in the range between 0.05 mm and 1 mm and is preferably at most 0.8 mm, more preferably at most 0.6 mm, still more preferably at most 0.4 mm and for example 0.2 mm.

The shaft portion 29 lies flat against the collar 28 on the side thereof facing away from the heating body 60. The real or imaginary separating surface between the collar 28 and the shaft portion 29 can lie in one plane with the surface of the support 23 facing the heating body 60. The shaft portion 29 can in particular designate the remaining part of the wick structure 19, apart from the collar 28. In the free, pre-assembled state, the shaft portion 29 can have an oversize, i.e. a larger diameter than the passage opening 25 in order to generate additional holding forces of the shaft 29 in the passage opening 25.

Figure 8:
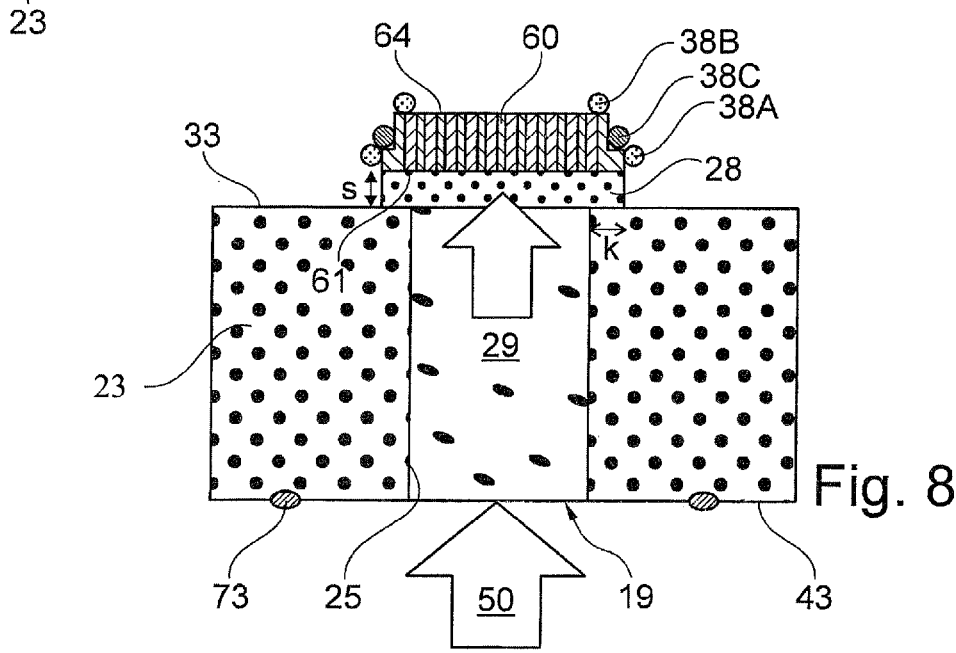

The collar 28 and the shaft 29 can be formed in one piece or integrally, see FIG. 8. A collar 28 and a shaft 29 can also each be separate parts and be formed by corresponding wick portions 35, 36, see FIG. 6. FIG. 3 illustrates that the collar 28 and/or the shaft 29 can each be made of several parts and in each case can be formed by corresponding wick portions 55, 56 and 57, 58, respectively.

The diameter dc of the collar 28 (see FIG. 6) is larger than the diameter dp of the passage opening 25 and thus of the shaft 29 in the region of the passage opening 25. The collar 28 preferably protrudes over its entire circumference over the passage opening 25 with a protrusion k. The protrusion k of the collar 28 over the passage opening 25 is preferably at least 0.1 mm, more preferably at least 0.2 mm, even more preferably at least 0.3 mm and particularly preferably at least 0.4 mm.

Due to the protrusion of the collar 28 on all sides through the passage opening 25, when the heating body 60 is clamped onto the support 23, the collar 28, and thus the entire wick structure 19, is securely held in the evaporator unit 20.

Figure 4:
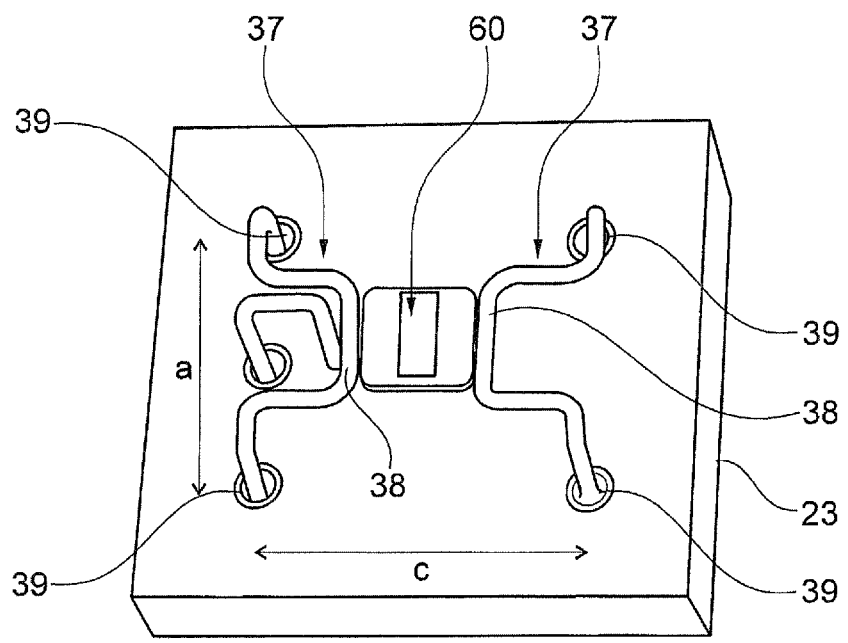
FIG. 4, 5 are a top view of the support of an evaporator unit from the side of the heating body (FIG. 4) and from the opposite side of the liquid supply (FIG. 5)
Figure 5:
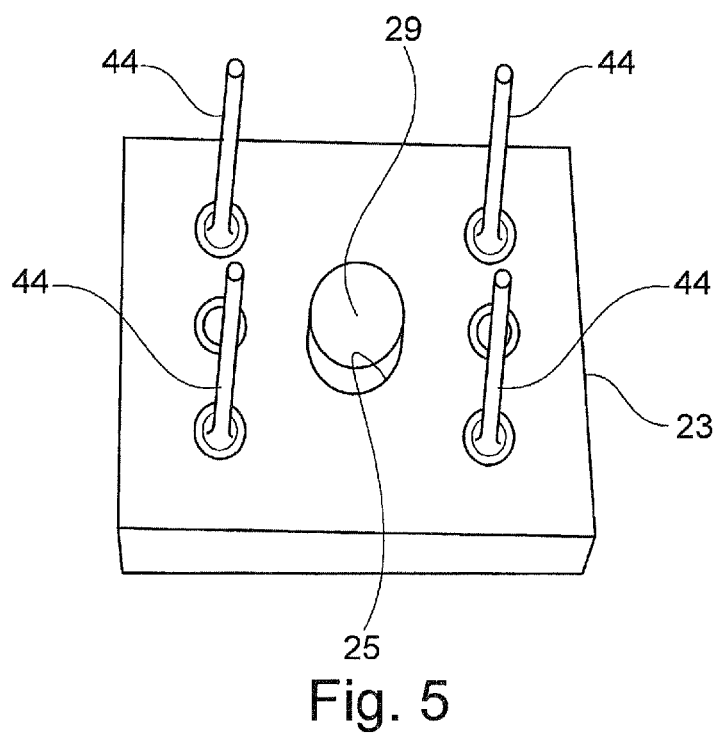

The heating body 60 is clamped on the support 23 by means of at least two clamping elements 37, see in particular FIG. 4, which engage the heating body 60 on opposite sides thereof. Each clamping element 37 advantageously has a clamping bracket 38 which is resiliently attached to the support 23 at two spaced-apart fastening points 39 and generates a pretension by means of which the heating body 60 and the collar 28 are clamped on the support 23.

The distance a between the two fastening points 39 of a clamping bracket 38 is preferably in the range between 4 mm and 10 mm, more preferably in the range between 5 mm and 8 mm and is, for example, 6 mm. The distance c between the fastening points 39 of two clamping brackets 38 from one another is preferably in the range between 5 mm and 12 mm, more preferably in the range between 6 mm and 10 mm and is, for example, 8 mm. The dimensions of the rectangular support 23, for example, are preferably in the range between 6 mm and 20 mm, more preferably in the range between 8 mm and 17 mm and even more preferably in the range between 10 mm and 14 mm.

The clamping elements 37 serve particularly advantageously at the same time as electrodes for contacting the heating body 60 and supplying it with heating current. For this purpose, the clamping elements 37 or the clamping brackets 38 advantageously consist of an electrically conductive material; for example this can be metal wire, for example brass wire. Due to the line contact between the clamping bracket 38 and the heating body 60, there is an excellent electrical connection between the clamping element 37 and the heating body 60, with at the same time ideal thermal decoupling between the clamping element 37 and the heating body 60 due to the lack of surface contact. Heat dissipation from the heating body 60 into the clamping element 37 is therefore low; the clamping brackets 38 remain significantly cooler than the heating body 60.

The clamping bracket 38 can clamp the heating body 60 laterally parallel to the outlet side 64 (clamping bracket 38A in FIG. 6) and/or perpendicularly to the outlet side 64 (clamping bracket 38B in FIG. 6) and/or in a groove or step with an intermediate angle, for example between 30° and 60°, both laterally and vertically onto the outlet side 64 (clamping bracket 38C in FIG. 6). The latter possibility involves two contact lines between the clamping bracket 38C and the heating body 60, which further improves the electrical contacting. A clamping element 37 can also have more than one clamping bracket 38, in particular any two or all three of the clamping brackets 38A, 38B, 38C.

The clamping elements 37 are advantageously connected by means of electrical lines 12 to a printed circuit board 26 (PCB) provided in the consumption unit 17 in order to establish the electrical connection to the electronic control device 15 and to the energy source for the power supply of the heating body 60. Electronic components of the consumption unit 17 are advantageously arranged on the printed circuit board 26.

In the embodiment according to FIG. 3, the printed circuit board 26 is a separate part and is spaced apart from the support 23 on the under side 43 thereof facing away from the heating body 60. The printed circuit board 26 has a passage opening 27 through which the shaft 29 of the wick structure 19 extends and in which the wick structure 19 can be held. The electrical lines 12 here include, for example, four metal pins 44, which are connected on the upper side 33 of the support 23 in the fastening points 39 to the clamping elements 37 and in each case extend through a through-hole 45 through the support 23 and then bridge the distance between the support 23 and the printed circuit board 26 on the under side 43 facing away.

In another embodiment, the support 23 can form the printed circuit board 26. The electrical lines 12 can then be omitted. It is also possible that the evaporator unit 20 itself does not comprise a printed circuit board, but rather the clamping brackets 38 are connected to a printed circuit board arranged approximately in the base part 16, for example via flexible insulated lines, or in another suitable manner.

A recess 74 adapted to the collar 28 can be provided on the upper side 33 of the support 23, into which the collar 28 can be inserted with a precise fit during assembly in order to define an optimal assembly position of the collar 28.

A sealing element 73, for example a sealing ring, can be arranged on the underside 43 of the support 23 to seal the support 23 against a housing of the liquid store 18 or another component arranged under the support 23, see FIGS. 6 and 8.

The activation frequency of the heating body 60 produced by the heating voltage source 71 is generally advantageously in the range from 1 Hz to 50 kHz, preferably in the range from 30 Hz to 30 kHz, and even further advantageously in the range from 100 Hz to 25 kHz.

The course of the evaporation procedure is explained below.

In an initial state, the heating voltage source 71 for the heating procedure is switched off.

To evaporate liquid 50, the heating voltage source 71 for the heating body 60 is activated. The voltage Uh is set in such a manner that the evaporation temperature in the heating body 60 and therefore in the microchannels 62 is adapted to the individual evaporation behaviour of the liquid mixture used. This prevents the danger of local overheating and thereby the formation of harmful substances.

As soon as a quantity of liquid equal to or related to the volume of the microchannels 62 has evaporated, the heating voltage source 71 is deactivated. Since the liquid properties and amount are advantageously known exactly, this point in time can be controlled very precisely. The energy consumption of the evaporator unit 20 can therefore be reduced compared to known devices, since the required evaporation energy can be dosed and thereby introduced more precisely. Due to the design of the heating body 60, this can also be referred to as a volume evaporator, in contrast to conventional surface evaporators.

After completion of the heating procedure, the microchannels 62 are predominantly or completely emptied. The heating voltage 71 is then kept switched off until the microchannels 62 are replenished by transferring liquid through the wick structure 19. When this happens, the next heating cycle can be started by switching on the heating voltage source 71.

EMBODIMENTS

Embodiment 1. Evaporator unit for an inhaler, in particular for an electronic cigarette product, comprising an electrically operable heating body (60), in particular a flat heating body, which has an inlet side (61) and an outlet side (64), a support (23) for supporting the heating body, and a plurality of microchannels (62), each of which extends from the inlet side (61) to the outlet side (64) through the heating body (60), wherein the heating body (60) is designed to evaporate liquid being transferred through the microchannels (62) by applying a heating voltage, characterised in that a porous and/or capillary wick structure (19) is arranged on the inlet side (61) of the heating body (60), said wick structure being fluidically connected or connectable to a liquid store (18), wherein the wick structure (19) has a shaft which extends through a passage opening (25) of the support (23), and a collar (28), which is arranged between the support (23) and the heating body (60), wherein the diameter of the collar (28) is greater than the diameter of the passage opening (25) of the support (23).

Embodiment 2. Evaporator unit according to embodiment 1, characterised in that the evaporator unit (20) has at least one clamping element (37) which generates a pretension and which is arranged and set up for clamping the heating body (60) and the collar (28) onto the support (23).

Embodiment 3. Evaporator unit according to embodiment 2, characterised in that at least two clamping elements (37) are provided on opposite sides of the heating body (60).

Embodiment 4. Evaporator unit according to either embodiment 2 or embodiment 3, characterised in that the at least one clamping element (37) has a clamping bracket (38) which makes linear contact with the heating body (60).

Embodiment 5. Evaporator unit according to any of embodiments 2 to 4, characterised in that the at least one clamping element (37) clamps the heating body (60) laterally parallel to the outlet side and/or perpendicularly to the outlet side (64) and/or in a groove or step of the support (23).

Embodiment 6. Evaporator unit according to any of embodiments 2 to 5, characterised in that the at least one clamping element (37) serves as an electrode for electrically contacting and supplying the heating body (60).

Embodiment 7. Evaporator unit according to embodiment 6, characterised in that at least one conductor (12) extending through a bore (45) in the support (23) is provided for contacting the clamping element (37).

Embodiment 8. Evaporator unit according to embodiment 7, characterised in that the at least one conductor (12) contacts a printed circuit board (26) which is arranged at a distance on the side of the support (23) facing away from the heating body (60).

Embodiment 9. Evaporator unit according to any of the preceding embodiments, characterised in that the support (23) is designed as a printed circuit board (23).

Embodiment 10. Evaporator unit according to any of the preceding embodiments, characterised in that the collar (28) protrudes over its entire circumference through the passage opening (25) of the support (23).

Embodiment 11. Evaporator unit according to embodiment 10, characterised in that the all-round protrusion k of the collar (28) through the passage opening (25) of the support (23) is at least 0.1 mm.

Embodiment 12. Evaporator unit according to any of the preceding embodiments, characterised in that the transfer rate of the wick structure (19) is at least as large as the maximum evaporation rate of the heating body (60).

Embodiment 13. Evaporator unit according to any of the preceding embodiments, characterised in that the wick structure (19) consists advantageously of one or a plurality of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, or a combination of two or a plurality of the materials mentioned above.

Embodiment 14. Evaporator unit according to any of the preceding embodiments, characterised in that the wick structure (19) has a filter layer (55), in particular made of micro-glass fibre.

Embodiment 15. Evaporator unit according to any of the preceding embodiments, characterised in that the wick structure (19) has a fibre paper and/or a ceramic paper layer (35; 56).

Embodiment 16. Evaporator unit according to any of the preceding embodiments, characterised in that the wick structure (19) has a porous ceramic layer (36; 57).

Embodiment 17. Evaporator unit according to any of the preceding embodiments, characterised in that the wick structure (19) has an oil lamp wick layer (58).

The evaporator unit 20 is preferably produced on the basis of MEMS technology, in particular from silicon, and is therefore advantageously a micro-electromechanical system.

The invention claimed is:

1. An evaporator unit for an inhaler, comprising:
an electrically operable heating body, which has an inlet side and an outlet side;
a support for supporting the electrically operable heating body; and
a plurality of microchannels, each of which extends from the inlet side to the outlet side through the electrically operable heating body,
wherein the electrically operable heating body is configured to evaporate liquid being transferred through the plurality of microchannels by applying a heating voltage,
wherein a porous and/or capillary wick structure is arranged on the inlet side of the electrically operable heating body,
wherein the wick structure is fluidically connectable to a liquid store,
wherein the wick structure comprises a shaft which extends through a passage opening of the support; and
a collar, which is arranged between the support and the electrically operable heating body, wherein a diameter of the collar is greater than a diameter of the passage opening of the support, wherein when the wick structure is fluidically connected to the liquid store, fluid is passively transported from the liquid store via the wick structure, through the passage opening of the support via the shaft of the wick structure, to the inlet side of the electrically operable heating body via the collar of the wick structure.

2. The evaporator unit according to claim 1, further comprising:
at least one clamping element which generates a pretension and which is arranged and set up for clamping the electrically operable heating body and the collar onto the support.

3. The evaporator unit according to claim 2, wherein the at least one clamping element comprises at least two clamping elements provided on opposite sides of the electrically operable heating body.

4. The evaporator unit according to claim 2, wherein the at least one clamping element has a clamping bracket that makes linear contact with the electrically operable heating body.

5. The evaporator unit according to claim 2, wherein the at least one clamping element clamps the electrically operable heating body laterally parallel to the outlet side and/or perpendicularly to the outlet side and/or in a groove or step of the support.

6. The evaporator unit according to claim 2, wherein the at least one clamping element serves as an electrode for electrically contacting the electrically operable heating body and supplying heating current to the electrically operable heating body.

7. The evaporator unit according to claim 6, wherein at least one conductor extending through a bore in the support is provided for contacting the at least one clamping element.

8. The evaporator unit according to claim 7, wherein the at least one conductor contacts a printed circuit board that is arranged at a distance on the side of the support facing away from the electrically operable heating body.

9. The evaporator unit according to claim 1, wherein the support is designed as a printed circuit board.

10. The evaporator unit according to claim 1, wherein the collar protrudes over an entire circumference of the collar over the passage opening of the support.

11. The evaporator unit according to claim 10, wherein an all-round protrusion of the collar over the passage opening of the support is at least 0.1 mm.

12. The evaporator unit according to claim 1, wherein a transfer rate of the wick structure is at least as large as a maximum evaporation rate of the electrically operable heating body.

13. The evaporator unit according to claim 1, wherein the wick structure comprises one or more of the following materials: cotton, cellulose, acetate, glass fibre fabric, glass fibre ceramic, sintered ceramic, ceramic paper, aluminosilicate paper, metal foam, metal sponge, another heat-resistant, porous and/or capillary material having a suitable transfer rate, or a combination of two or more of the listed materials.

14. The evaporator unit according to claim 1, wherein the wick structure has a filter layer made of micro-glass fibre.

15. The evaporator unit according to claim 1, wherein the wick structure has a fibre paper and/or a ceramic paper layer.

16. The evaporator unit according to claim 1, wherein the wick structure has a porous ceramic layer.

17. The evaporator unit according to claim 1, wherein the wick structure has an oil lamp wick layer.

18. The evaporator unit according to claim 1, wherein the electrically operable heating body is a flat heating body.

19. An electronic cigarette product, comprising:
the evaporator unit according to claim 1.

* * * * *